United States Patent [19]

Hatano et al.

[11] 4,356,265

[45] Oct. 26, 1982

[54] METHOD FOR THE PRODUCTION OF ANTIBIOTIC C-15003 P-3

[75] Inventors: Kazunori Hatano, Kawanishi; Masanari Nakamichi, Amagasaki; Shun-ichi Akiyama, Fujisawa, all of Japan

[73] Assignee: Takeda Chemical Industries, Ltd., Osaka, Japan

[21] Appl. No.: 209,983

[22] Filed: Nov. 24, 1980

[30] Foreign Application Priority Data

Dec. 28, 1979 [JP] Japan .................................. 54-173819

[51] Int. Cl.$^3$ .............................................. C12P 17/18
[52] U.S. Cl. .................................... 435/119; 435/244; 435/872
[58] Field of Search ........................ 435/119, 128, 244

[56] References Cited

U.S. PATENT DOCUMENTS

| 3,795,585 | 3/1974 | Suzuki et al. ................. 435/244 X |
| 4,162,940 | 7/1979 | Higashide et al. ............. 435/119 |
| 4,228,239 | 10/1980 | Higashide et al. ............. 435/119 |
| 4,229,533 | 10/1980 | Higashide et al. ............. 435/119 |

*Primary Examiner*—Lionel M. Shapiro
*Attorney, Agent, or Firm*—Wegner & Bretschneider

[57] ABSTRACT

Antibiotic C-15003 P-3 is specifically produced by cultivating a microorganism belonging to the genus Nocardia in a culture medium to which isobutyl aldehyde, isobutyl alcohol or a fatty acid ester of isobutyl alcohol is added.

The Antibiotic C-15003 P-3 is useful as an antifungal, antiprotozoan or antitumor agent.

6 Claims, No Drawings

METHOD FOR THE PRODUCTION OF ANTIBIOTIC C-15003 P-3

This invention relates to a method for producing Antibiotic C-15003 P-3 in an industrially advantageous method.

Antibiotic C-15003 P-3 [hereinafter, it is abbreviated as "P-3"] is a compound obtained by cultivating a microorganism of the genus Nocardia, which is isolated from natural resources for example soil sample and so on.

The compound and the production thereof are described in U.S. Pat. No. 4,162,940 in detail. The known process produces several components of Antibiotic C-15003 simultaneously. For separating each component from the cultured broth, very complicated processes are required, and said process is not an advantageous one in view of the yield of the desired compound.

With the purpose of overcoming this drawback, the present inventors have made extensive study, especially, for recovering P-3 specifically, and found that an addition of isobutyl alcohol and/or isobutyl aldehyde into the culture medium in which a microorganism belonging to the genus Nocardia is cultivated causes the accomplishment of the purpose. The present invention is based on the above finding.

The present invention is a method for producing and accumulating Antibiotic C-15003 P-3 which comprises cultivating a microorganism belonging to the genus Nocardia which is capable of producing antibiotic C-15003 [hereinafter sometimes called "Antibiotic C-15003-producing strain"] in a culture medium, said culture medium including a member selected from the group consisting of isobutyl aldehyde, isobutyl alcohol and a fatty acid ester of isobutyl alcohol.

In the context of this invention, the term "Antibiotic C-15003" or "C-15003" means, generically, the four compounds having the following general formula (I) as a group, or a mixture of two or more of said compounds or, severally, any one of the same compounds.

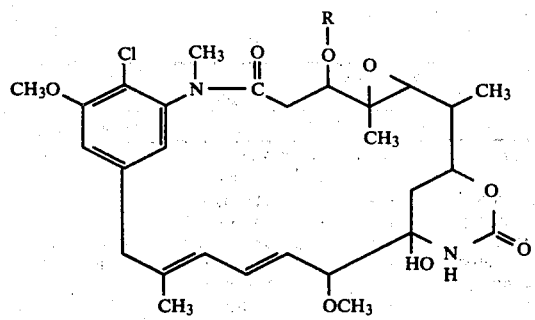

wherein R represents

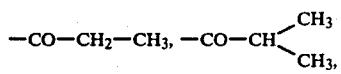

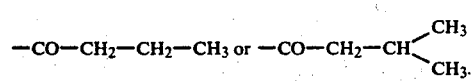

Referring, also, to the general formula (I), the compound in which R is —CO—CH$_2$—CH$_3$ is referred to herein as "Antibiotic C-15003 P-2" or more briefly as "P-2"; the compound in which R is

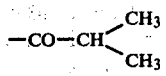

is referred to herein as "Antibiotic C-15003 P-3" or more briefly as "P-3"; the compound in which R is —CO—CH$_2$—CH$_2$—CH$_3$ is referred to herein as "Antibiotic C-15003 P-3'" or, more briefly, as "P-3'"; the compound in which R is

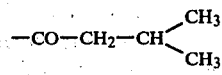

is referred to herein as "Antibiotic C-15003 P-4" or, more briefly, as "P-4".

As an example of the microorganism employable in the present invention, there may be mentioned an actinomycete Strain No. C-15003 [Nocardia sp. No. C-15003; hereinafter sometimes abbreviated as "Strain No. C-15003"] which was isolated from soil or other samples.

The present Strain No. C-15003 has been deposited at Fermentation Research Institute, Agency of Industrial Science and Technology (FERM), Japan under FERM-P No. 3992 as from Mar. 23, 1977; at The Institute for Fermentation, Osaka (IFO), Japan under the number of IFO 13726 as from Mar. 22, 1977 and at The American Type Culture Collection (ATCC), Maryland, U.S.A. under the number of ATCC 31281 as from Mar. 31, 1977. The strain Nocardia sp. No. C-15003 (ATCC 31281) is described in The American Type Culture Collection Catalogue of Strains I Fourteenth Edition (1980).

The microbiological characters of Strain No. C-15003 are described in U.S. Pat. No. 4,162,940.

That is to say, the microbiological characters of Strain No. C-15003 are investigated by procedures analogous to those proposed by Schirling & Gottlieb [International Journal of Systematic Bacteriology, 16, 313-340 (1966)]. The results of observations at 28° C. over 21 days are as follows:

(1) Morphological characters:

The vegetative mycelium extends well and develops into branches, both on agar and in liquid medium. Many of the hyphae measure 0.8 to 1.2 $\mu$m in diameter and, in certain instances, may divide into fragments resembling rod bacteria or branched hyphae of short length. The strain gives good growth on various taxonomical media, with aerial mycelium being superimposed on the vegetative mycelium, although it frequently forms coremia like bodies (50–200×200—1000 $\mu$m) on which further aerial growth takes place. Many of the aerial mycelia are flexuous, straight or a loosely spiral like configuration being encountered on a few occasions. Microscopic examination of aged cultures reveals that only in few cases the conidia like cells occur in chains, while the cell suspensions obtained from the surfaces of such cultures, as microscopically examined, contained many elongated ellipsoidal (0.8–1.2 $\mu$m×4.8–6.3 $\mu$m) and ellipsoidal (0.8–1.2×1.0–2.0 $\mu$m) bodies resembling arthrospores.

Electron-microscopic examinations shows that these bodies had smooth surfaces.

(2) The constituents of cells:

The strain was shake-cultured in modified ISP No. 1 medium at 28° C. for 66 to 90 hours, at the end of which time the cells were collected and rinsed. By the method of B. Becker et al. [Applied Microbiology, 12, 421 (1964)] and the method of M. P. Lechevalier [Journal of Laboratory and Clinical Medicine, 71, 934 (1968)], the above whole cells were examined for diaminopimelic acid and sugar composition. The former was found to be the meso-form, while spots were detected which corresponded to galactose and arabinose.

(3) Characteristics on taxonomical media:

The strain showed comparatively good growth on various media, with the vegetative mycelium being colorless to pale yellow in initial phases of culture and light yellowish tan to yellowish tan in later phases. The strain produces soluble pigments, yellow to yellowish tan, in various taxonomical media. The aerial mycelium is powdery and generally gives moderate growth, being white to yellow or light yellowish tan. The characteristics of the strain in various taxonomical media are set forth in Table 1.

TABLE 1

Cultural characteristics of Strain No. C-15003 on taxonomical media (A) Sucrose nitrate agar:
　　Growth (G): Moderate, Brite Melon Yellow (3 ia)*
　　　　to Amber tan (3 ic)*, coremia like bodies formed
　　Aerial mycelium
　　　　(AM): Scant, white
　　Soluble pigment
　　　　(SP): None or pale yellowish tan
(B) Glycerol nitrate agar:
　　　　G: Moderate, Lt Ivory (2 ca)*, coremia like bodies formed
　　　　AM: Moderate, white
　　　　SP: None
(C) Glucose asparagine agar:
　　　　G: Moderate, Brite Marigold (3 pa)* to Brite Yellow (2 pa)*
　　　　AM: Scant, white
　　　　SP: Brite Yellow (2 pa)*
(D) Glycerol asparagine agar:
　　　　G: Moderate, Lt Ivory (2 ca)*, coremia like bodies formed
　　　　AM: Scant, white
　　　　SP: None
(E) Starch agar:
　　　　G: Moderate, Lt Ivory (2 ca)* to Lt Wheat (2 ea)* coremia like bodies formed
　　　　AM: Abundant, Lt Ivory (2 ca)*
　　　　SP: None
(F) Nutrient agar:
　　　　G: Moderate, Lt Ivory (2 ca)* to Colonial Yellow (2 ga)*, coremia like bodies formed
　　　　AM: Scant, white
　　　　SP: None
(G) Calcium malate agar:
　　　　G: Moderate Lt Ivory (2 ca)* to Lt Wheat (2 ea)*, coremia like bodies formed
　　　　AM: Moderate, white to Lt Ivory (2 ca)*
　　　　SP: None
(H) Yeast extract-malt extract agar:
　　　　G: Moderate, Amber (3 lc)* to Brite Yellow (3 la)*, coremia like bodies formed
　　　　AM: Moderate, white to Lt Ivory (2 ca)*
　　　　SP: None
(I) Oatmeal agar:
　　　　G: Moderate, Lt Ivory (2 ca)* to Colonial Yellow (2 ga)*, coremia like bodies formed
　　　　AM: Scant, white to light yellow
　　　　SP: None
(J) Peptone yeast extract iron agar:
　　　　G: Moderate, Colonial Yellow (2 ga)*
　　　　AM: None

TABLE 1-continued

Cultural characteristics of Strain No. C-15003 on taxonomical media

SP: Colonial Yellow (2 ga)*
(K) Tyrosine agar
　　　　G: Moderate, Lt Ivory (2 ca)* to Lt Melon Yellow (3 ea)*, coremia like bodies formed
　　　　AM: Moderate, white to Lt Ivory (2 ca)*
　　　　SP: Camel (3 ie)*

*The color codes according to Color Harmony Manual, 4th Ed. (Container Corporation of America, 1958).

(4) Physiological characters:

The physiological characters of the strain are shown in Table 2. Temperature range for growth: 12° C. to 38° C. The temperature range in which good aerial growth occurs on agar (ISP No. 2) is 20° to 35° C.

TABLE 2

The physiological characters of Strain No. C-15003

| | |
|---|---|
| Temperature range for growth: | 12 to 38° C. |
| Temperature range for aerial growth: | 20 to 35° C. |
| Liquefaction of gelatin: | Positive |
| Hydrolysis of starch: | Positive |
| Reduction of nitrates: | Positive |
| Peptonization of milk: | Positive |
| Coagulation of milk: | Negative |
| Decomposition of casein: | Positive |
| Production of melanoid pigments: | Negative (peptone yeast extract iron agar), Positive (tyrosine agar) |
| Decomposition of tyrosine: | Positive |
| Decomposition of xanthine: | Negative |
| Decomposition of hypoxanthine: | Negative |
| Tolerance to lysozyme: | Positive |
| Tolerance to sodium chloride: | 2% |

(5) Utilization of various carbon sources

The utilization of various carbon sources was investigated using a medium described in Pridham and Gottlieb [Journal of Bacteriology, 56, 107 (1948)] and a basal medium of the same composition plus 0.1% of yeast extract (Bacto). The resultant spectrum is shown in Table 3.

TABLE 3

The utilization of carbon sources by Strain No. C-15003

| Source of carbon | Growth | | Sources of carbon | Growth | |
|---|---|---|---|---|---|
| D-Xylose | + | ++* | Raffinose | ± | ±* |
| L-Arabinose | + | + | Melibiose | + | + |
| D-Glucose | ++ | ++ | i-Inositol | − | − |
| D-Galactose | + | + | D-Sorbitol | − | − |
| D-Fructose | +++ | ++ | D-Mannitol | ++ | ++ |
| L-Rhamnose | + | + | Glycerol | + | ± |
| D-Mannose | +++ | ++ | Soluble starch | + | + |
| Sucrose | ++ | ++ | Control | − | − |
| Lactose | − | − | | | |
| Maltose | ± | + | | | |
| Trehalose | + | ++ | | | |

*Basal medium with 0.1% yeast extract added
Note:
+++: Luxuriant growth
++: Good growth
+: Growth
±: Poor growth
−: No growth (6) Other characteristics The cells were harvested by the procedure previously described in (2) and DNA was prepared by a procedure analogous to that of J. Marmur et al. [Journal of Molecular Biology, 3, 208, (1961)]. The G-C (guaninecytosine) content of the DNA was found to be about 71 mole %.

Gram-staining of the vegetative mycelium of this strain was positive.

The above characteristics of Strain No. C-15003 were compared with the descriptions in S. A. Waksman's "The Actinomycetes Vol. 2" [The Williams and Wilkins Co., 1961]; R. E. Buchanan and N. E. Gibbons, "Bergey's Manual of Determinative Bacteriology, 8th Ed, 1974"; and other literatures.

Whilst this strain was thought to belong to Group III of the genus Nocardia, the failure to find any species having the characters so far described among the known strains led us to conclude that this strain represented a novel species of microorganism.

While a microorganism of the genus Nocardia is liable, as are microorganisms generally, to undergo variations and mutations artificially. For example, the many variants of the strain which are obtainable by irradiation with X-ray, ultraviolet light, or by chemical treatment with chemicals (e.g. nitrosoguanidine, ethyleneimine). Any of such variants and mutants capable of producing Antibiotic C-15003 may be invariably employed in the purposes of this invention.

Isobutyl alcohol its fatty acid ester and/or isobutyl aldehyde are/is added into the culture medium either independently or simultaneously. The amount of addition of the above substances(s) is generally not less than about 0.005 volume/volume percent based on the volume of the culture medium as the amount of the single compound or the total amount of the three compounds, provided that the addition amount of the fatty acid ester is shown in terms of isobutyl alcohol. And it is preferable that about 0.01 to about 0.5 volume/volume percent of isobutyl alcohol, its fatty acid ester and/or isobutyl aldehyde are/is added into the culture medium based on the volume of the culture medium. However, the amount of the addition of the substance(s) may be increased so long as the substance(s) does/do not inhibit the growth of the microorganism used or does/do not suppress the production of the desired antibiotic.

Isobutyl alcohol, its fatty acid ester and/or isobutyl aldehyde may be added into the culture medium before the inoculation of the C-15003-producing strain into the sterillized medium, or during the production of C-15003 is continued after the C-15003-producing strain is inoculated into the medium. As examples of the fatty acid esters of isobutyl alcohol there may be mentioned esters of fatty acids having 1 to 4 carbon atoms (e.g. formate, acetate, propionate, butyrate, isobutyrate) of isobutyl alcohol.

The medium employable for the cultivation of such an Antibiotic C-15003-producing strain may be whichever of a liquid and a solid medium only if it contains nutrients which the strain may utilize. For high-production runs a liquid medium is generally preferred. The medium may comprise the additive substance used in the present invention, carbon and nitrogen sources which Antibiotic C-15003-producing strain may assimilate and metabolize, inorganic substances, trace nutrients, etc. As examples of said carbon sources may be mentioned glucose, lactose, sucrose, molasses, maltose, dextrin, starch, glycerol, mannitol, sorbitol, etc., fats and oils (e.g. soybean oil, lard oil, chicken oil, etc.) and so forth. The nitrogen sources may for example be meat extract, yeast extract, dried yeast, soybean meal, corn steep liquor, peptone, cottonseed flour, urea, ammonium salts (e.g. ammonium sulfate, ammonium chloride, ammonium nitrate, ammonium acetate, etc.). The medium may further contain salts of sodium, potassium, calcium, magnesium, etc., metal salts of iron, manganese, zinc, cobalt, nickel, etc., salts of phosphoric acid, boric acid, etc. Further, the medium may contain, when desired, vitamins, nucleic acids and so forth. For the purpose of adjusting the pH of the medium, acids and/or alkalines may be added. Furthermore, proper amount of oils and fats or surfactants may also be added into the medium for defoaming.

The cultivation may be conducted by any of the stationary, shaking, aerobic submerged or other cultural conditions. For high production runs, aerobic submerged culture is of course preferable. While the conditions of culture, of course, depend upon the composition of the medium, the strain used, the cultural method and other factors, it is normally preferable to carry out incubation with an initial pH of about 5.5 to 8.0 or thereabouts, preferably with pH 6.5 to 7.5, at a temperature ranging from about 15° to 35° C., preferably from 20° to 30° C. The cultivation is conducted until the potency of P-3 becomes maximal. While the cultivation time is variable according to cultivation method, temperature, composition of medium, the cultivation time is generally about 48 to 240 hours.

In order to recover and purify thus specifically produced P-3 in the culture broth, it can be conveniently employed with separation and purification procedure which are ordinally employed for the recovery of such microbial metabolites. Because the desired product is lipophilic neutral substance, the product is easily extracted from the cultured broth or culture filtrate with water-immiscible organic solvents such as fatty acid esters (e.g. ethyl acetate, amyl acetate), alcohols (e.g. butanol), halogenated hydrocarbons (e.g. chloroform) and ketones (e.g. methyl isobutyl ketone). The extraction is carried out at a pH near neutral, preferably with ethyl acetate at pH 7. The extract is washed with water and concentrated under reduced pressure. Then, a nonpolar solvent such as petroleum ether or hexane is added to the concentrate and the crude product containing the active compounds is recovered as precipitates. The crude product is sequentially subjected to convenient purification procedures. Thus, as a routine purification procedure, adsorption chromatography is useful and, for this purpose, one of those common adsorbents such as silica gel, active alumina, macroporous-nonionic adsorbent resin, etc., may be employed. P-3 in the crude product is developed on such silica-gel chromatography with, for example, petroleum ether or hexane and eluted by the addition of a polar solvent such as ethyl acetate, acetone, ethanol or methanol, or a halogenated hydrocarbon such as dichloromethane or chloroform containing a polar solvent such as an alcohol (e.g. methanol, ethanol), a ketone (e.g. acetone, methyl ethyl ketone), or the like. In this way, P-3 is eluted, separated and recovered.

In the case that a macroporous adsorbent resin is used for the purification of P-3, elution of P-3 from the column is accomplished with a mixture of water with a lower alcohol, a lower ketone or an ester. The lower alcohol may, for example, be methanol, ethanol, propanol or butanol, etc., and the lower ketone may for example be acetone or methyl ethyl ketone, etc. The ester may for example be ethyl acetate, etc. In a typical procedure, the crude product is dissolved in 60% methanol-water and adsorbed on a column of Diaion HP-10 (Mitsubishi Chemical Industries, Ltd., Japan). The column is washed with 70% methanol-water and P-3 is eluted with 90% methanol-water.

In the process described above, the fractions containing P-3 are pooled and concentrated under reduced pressure. To the dry product is added 5 to 8 volumes of ethyl acetate and the mixture is allowed to stand, whereupon P-3 is crystallized out.

The physico-chemical properties of the Antibiotic C-15003 P-3 is described in U.S. Pat. No. 4,162,940. That is to say, the physico-chemical properties of P-3 are shown in Table 4.

TABLE 4

Antibiotic C-15003 P-3 $C_{32}H_{43}ClN_2O_9 = 635.169$

| | |
|---|---|
| Melting point (°C.) | 190–192° |
| Specific rotation $[\alpha]_D^{22°}$ | $-136 \pm 10°$ (C=0.375 CHCl$_3$) |
| Elemental analysis Found (%) | C 60.06 |
| | H 7.04 |
| | N 4.33 |
| | Cl 5.37 |
| Elemental analysis Calcd. (%) | C 60.51 |
| | H 6.82 |
| | N 4.41 |
| | Cl 5.58 |
| Ultraviolet absorption spectra nm($\epsilon$) (in methanol) | 233(30250), 240(sh 28450), 252(27640), 280(5750), 288 (5700). |
| Infrared absorption spectra (cm$^{-1}$)KBr | 1740, 1730, 1670, 1580, 1445, 1385, 1340, 1255, 1180, 1150, 1100, 1080. |
| Nuclear magnetic resonance spectra (ppm) 100 MHz in CDCl$_3$ | 1.27(d) (3H), 1.28(d) (3H). |
| Mass spectra (m/e) | 573, 485, 470, 450 |
| Solubility | Insoluble in petroleum ether, n-hexane, water. Sparingly soluble in benzene, ether. Soluble in chloroform, ethyl acetate, acetone, ethanol, methanol, pyridine, tetrahydrofuran, dimethylsulfoxide |
| Color reactions | Dragendorff: Positive Beilstein: Positive |

In the present invention, the production ratio of P-3 among Antibiotic C-15003 is very high, and the production amount of P-3 is increased. Since the present method causes advantageous features that the production amount of the desired compound is high, the recovery and the purification of the desired compound are easy and the raw material is cheap and is a liquid, and the present method does not cause the defects that a bad smell of isobutyric acid and erosion of the apparatus are emerged. And the present method has an advantageous feature that the toxicities of isobutyl alcohol and isobutyl aldehyde to the C-15003-producing strain is low. Therefore, the present method is an advantageous one for the industrial production of P-3.

Antibiotic C-15003 P-3 has biological activities and usages as described in U.S. Pat. No. 4,162,940. That is to say, the activities and usages of P-3 are as follows:

(A) Antimicrobial activity:

With Trypticase Soy Agar (manufactured by Baltimore Biological Laboratories, U.S.A.) as an assay medium, the inhibitory concentrations against the microorganisms described below are investigated by the paper disc method. Paper discs (Tōyō Seisakusho, thin-type, 8 mm in diam.) each impregnated with 0.02 ml of a 300-μg/ml solution of C-15003 P-3 are placed on agar plates respectively inoculated with the microorganisms described below. C-15003 P-3 has no activity against the following bacteria: *Escherichia coli, Proteus vulgaris, Proteus mirabilis, Pseudomonas aeruginosa, Staphylococcus aureus, Bacillus subtilis, Bacillus cereus, Klebsiella pneumoniae, Serratia, marcescens* and *Mycobacterium avium*.

On the other hand, the growth of a fungus, *Talaromyces avellaneus,* is inhibited by C-15003 P-3 on an agar plate consisting of 3.5 g disodium hydrogen phosphate, 0.5 g potassium dihydrogen phosphate, 5 g yeast extract (Difco), 10 g glucose, 15 g agar, 1000 ml distilled water, pH 7.0. The minimal inhibitory concentration is 3 μg/ml for C-15003 P-3.

Furthermore, *Tetrahymena pyriformis* W as an assay organism is cultivated on an assay medium [composed of 20 g Proteose-Peptone (Difco), 1 g yeast extract, 2 g glucose, 1000 ml distilled water and 10 ml phosphate buffer (1 M)], pH 7.0, at 28° C. for 44 to 48 hours and the growth inhibitory activity of C-15003 P-3 against the protozoa is determined by serial dilution method. Growth inhibition occurrs at 1 μg/ml.

(B) Antitumour activity:

The therapeutic effects of C-15003 P-3 (dosed intraperitoneally for 9 consecutive days) upon P388 leukemia cells in mice ($1 \times 10^6$ cells/animal, mouse, intraperitoneally transplanted) is investigated. C-15003 P-3 has an antitumour activity as high as 200% life-span-extending ratio at the dose level of 0.00625 mg/kg/day.

(C) Toxicity:

In a preliminary acute toxicity test with mice as test animals, which involved intraperitoneal injection of C-15003 P-3, this antibiotic shows that LD$_{100}$ value is 0.625 mg/kg and LD$_0$ value is 0.313 mg/kg.

As mentioned hereinbefore, C-15003 P-3 has strong inhibitory activity against fungi and protozoa and, therefore, is of value as an antifungal or antiprotozoan agent. Furthermore, because C-15003 P-3 displays a life-span-extending action upon tumour-bearing mammalian animals (e.g. mouse), it is also expected that the compound will be of use as an antitumour drug.

The present Antibiotic P-3, as an antifungal and antiprotozoan agent, can be used as a reagent with advantage for an assessment of the bacterial ecology in soil, active sludge, animal body fluid or the like. Thus, when valuable bacteria are to be isolated from soil samples or when the actions of bacteria are to be evaluated independently of those of fungi and protozoa in connection with the operation and analysis of an active sludge system used in the treatment of waste water, the present antibiotic may be utilized to obtain a selective growth of the bacterial flora without permitting growth of the concomitant fungi and protozoa in the specimen. In a typical instance, the sample is added to a liquid or solid medium and 0.1 ml of a 10 to 100 μg/ml solution of P-3 in 1% methanol-water is added per ml of the medium, which is then incubated.

As described in U.S. Pat. No. 4,162,940, P-3 has antifungi activity. That is to say, anti-fungal activity is shown in Table 5. As seen from Table 5, P-3 has growth inhibitory activity against microorganisms which cause plant diseases. The paper discs impregnated with 0.02 ml of a 1000 μg/ml solution of P-3 are placed on plates respectively inoculated with the microorganisms as following Table 5.

TABLE 5

Anti-microbial spectra

| Test organism | IFO number | Medium | Hour | Inhibition diameter (mm) |
|---|---|---|---|---|
| Alternaria kikuchiana | 7515 | PSA* | 48 | 38 |
| Fusicladium levieri | 6477 | PSA* | 90 | 68 |
| Helminthosporium sigmoideum var. irregulare | 5273 | PSA* | 48 | 55 |
| Pyricularia oryzae | — | PSA* | 48 | 53 |
| Elsinoe fawcetti | 8417 | PSA* | 90 | 55 |
| Fusarium oxysporum f. cucumerinum | — | PSA* | 48 | 20 |
| Guignardia laricina | 7888 | PSA* | 48 | 12 |
| Cochlioborus miyabeanus | 5277 | PSA* | 48 | 60 |
| Diaporthe citri | 9170 | PSA* | 48 | 55 |
| Gibberella zeae | 8850 | PSA* | 48 | 37 |
| Sclerotinia sclerotiorum | 9395 | PSA* | 90 | 65 |
| Venturia pirina | 6189 | PAA* | 48 | 50 |
| Pellicularia sasakii | 9253 | PSA* | 48 | 50 |
| Pythium aphanidermatam | 7030 | PSA* | 48 | 58 |
| Botrytis cinerea | — | PSA* | 48 | 48 |
| Aspergillus niger | 4066 | PSA* | 48 | 0 |
| Penicillium chrysogenum | 4626 | PSA* | 48 | 35 |
| Rhizopus nigricans | 6188 | PSA* | 48 | 25 |
| Saccharomyces cerevisiae | 0209 | PSA* | 48 | 0 |
| Rhodotorula rubra | 0907 | PSA* | 48 | 28 |
| Trichophyton rubrum | 5467 | GB** | 48 | 38 |
| Trichophyton mentagrophytes | 7522 | GB** | 48 | 38 |
| Candida albicans | 0583 | GB** | 48 | 0 |
| Candida utilis | 0619 | GB** | 48 | 0 |
| Cryptococcus neoformans | 0410 | GB** | 48 | 43 |

*PSA: Potato sucrose agar medium
**GB: Glocouse nutrient agar medium

P-3 can also be used as an anti-fungal agent for the treatment of plant diseases caused by the microorganisms mentioned in the above Table 5. In the typical application, P-3 is used in a form of 1% methanolic aqueous solution containing 0.5 μg/ml–5μg/ml of the antibiotic. For instance P-3 may be used for the control of the stem-rot, the Helminthosporium leaf spot and the sheath blight of rice plants.

The following examples are further illustrative to explain the present invention in detail. Percent (%) means weight/volume percent otherwise indicated.

EXAMPLE 1

Into 200-ml capacity of Erlenmeyer flask were poured 40 ml of a seed culture medium (1.0% glucose, 2.0% Bacto-Tryptone (Difco Laboratories, U.S.A.) and 1.2% Bacto-yeast extract (Difco Laboratories, U.S.A.), pH 7.0. After sterillization, Nocardia sp. No. C-15003 was inoculated into the medium. The inoculant was incubated at 28° C. for 48 hours on a rotary shaker (200 r.p.m.) to give a seed culture.

The seed culture was washed three times with sterillized distilled water, and the washed cells were re-slurred in the original volume with sterillized distilled water.

One milliliter of the above cell suspension was inoculated into 40 ml of main culture medium (3% soluble starch, 0.2% ammonium chloride, 0.05% magnesium sulfate, 1.09% potassium dihydrogen phosphate, 2.09% dipotassium hydrogen phosphate, 0.001% ferrous sulfate), and the cultivation was conducted at 28° C. for 48 hours on the rotary shaker.

After said cultivation, isobutyl aldehyde was added into the culture so as to make the content of isobutyl aldehyde 0.05% (volume/volume) in the medium, and the cultivation was carried out for six days.

After the completion of the cultivation, it was detected that the total production amount of Antibiotic C-15003 was 27 mg/l and the ratio of P-3 in the total was about 95% (weight/weight), but on the other hand, the ratio of P-3 in the total was 65% (weight/weight) without addition of isobutyl alcohol nor isobutyl aldehyde (Total production amount of Antibiotic C-15003: 10 mg/l).

The production amounts of the total Antibiotic C-15003 and of the respective ingredients were measured by means of the following procedure.

That is to say, the production amount of the total was measured by agar-well method employing Filobasidium uniguttulatum IFO 0699 as a test organism and a medium (pH 7.3) composed of 15 g of Trypticase-peptone (Baltimore Biologicals, U.S.A.), 5 g of Phytone peptone (Balitmore Biologicals, U.S.A.), 10 g of sodium chloride, 10 g of glucose, 15 g of agar and 1 l of distilled water. The production amount was calculated on the basis of the comparison of inhibition diameter by the test solution with that by standard solution.

The production amount and the ratio of P-3 were measured by the following manner: To the liquid sample containing the antibiotic was added the same volume of ethyl acetate, and the solution was subjected to extraction. The ethyl acetate layer was concentrated and dried, and the resulting residue was dissolved in ethyl acetate of an amount of 1/100 volume of the original volume to give a sample of thin-layer chromatography.

The solution thus obtained was applied to thin-layer chromatography of silica-gel 60 $F_{254}$ (E. Merck) glass plate using ethyl acetate saturated with water as a developing solvent.

The production amount and the production ratio of P-3 were measured by comparing with the density and expanse of the absorption band at 254 nm using Shimadzu Dual-wave length TLC-scanner, Model CS-910.

EXAMPLE 2

Five hundred milliliters of the seed culture medium as shown in Example 1 were poured into 2000-ml Sakaguchi flask and sterillized. The medium was inoculated with Nocardia sp. No. C-15003, and the medium was cultivated at 28° C. for 48 hours on a reciprocal shaker (110 s.p.m.) to give an inoculum.

In 200-l stainless steel fermentor were poured 100 l of a seed culture medium (2.0% glucose, 3.0% soluble starch, 1.0% corn steep liquor, 1.0% raw soybean flour, 0.5% Polypepton (Daigo Nutiritive Chemicals, Japan), 0.3% sodium chloride, 0.5% calcium carbonate, pH 7.0), the medium was sterillized at 121° C. for 20 minutes. After cooling, 500 ml of said inoculum were inoculated, and cultivation was carried out at 28° C. for 48 hours under aeration (100 l/minute) and agitation (200 r.p.m.).

The seed culture obtained as above was inoculated into 100 l of a main culture medium (5% dextrin, 3% corn steep liquor, 0.1% peptone, 0.5% calcium carbonate, pH 7.0) in the 200-l stainless steel fermentor and the cultivation was carried out at first at 28° C. for 48 hours under aeration (1 V.V.M.) and agitation (150 r.p.m.).

After 48-hour cultivation, isobutyl alcohol was added into the culture medium so as to make the amount of isobutyl alcohol in the medium 0.1% (volume/volume), and the cultivation was continued for 48 hours.

As the result, the production amount of total C-15003 was 20 mg/l and, the production amount of P-3 was 96% (weight/weight) in the total C-15003. Under the same conditions except for the addition of isobutyl alcohol to the culture, it brought 12 mg/l of total C-15003 and the production ratio of P-3 in the total of C-15003 was 65% (weight/weight).

EXAMPLE 3

A culture medium (40 ml) composed of 3% soluble starch, 0.2% ammonium chloride, 0.05% magnesium sulfate, 0.05% potassium chloride, 1.09% potassium dihydrogen phosphate, 2.09% dipotassium hydrogen phosphate and 0.001% ferrous sulfate was inoculated with 1 ml of the seed culture as of Example 1, and isobutyl alcohol or/and isobutyl aldehyde was/were added under the conditions shown in the Table 6. The cultivation at 28° C. for 8 days brought the results shown in Table 6.

TABLE 6

| Additive substance and concentration (v/v %) | | Time of of the addition | Total production amount (μg/ml) | Ratio of P-3 (%, w/w) |
|---|---|---|---|---|
| Isobutyl alcohol | 0.05% | 0 | 27 | 91 |
| Isobutyl alcohol | 0.05% | 48 | 29 | 95 |
| Isobutyl alcohol | 1.0% | 72 | 7 | 97 |
| Isobutyl aldehyde | 0.07% | 0 | 24 | 92 |
| Isobutyl aldehyde | 0.07% | 48 | 23 | 90 |
| Isobutyl aldehyde | 1.0% | 72 | 4 | 96 |
| Isobutyl alcohol | 0.04% | 48 | 28 | 94 |
| and isobutyl aldehyde | 0.01% | | | |
| Not added | | — | 10 | 58 |

EXAMPLE 4

In the manner as in Example 3, isobutyl alcohol or isobutyl aldehyde was added before the cultivation into the medium. The results shown in Table 7 were obtained.

TABLE 7

| Additive substance | Concentration (%, v/v) | Total production amount (μg/ml) | Ratio of P-3 (%, w/w) |
|---|---|---|---|
| Isobutyl alcohol | 0.01 | 24 | 74 |
| Isobutyl alcohol | 0.02 | 27 | 79 |
| Isobutyl alcohol | 0.05 | 27 | 92 |
| Isobutyl alcohol | 0.1 | 8 | 92 |
| Isobutyl alcohol | 0.2 | 2 | 95 |
| Isobutyl aldehyde | 0.01 | 18 | 75 |
| Isobutyl aldehyde | 0.02 | 21 | 79 |
| Isobutyl aldehyde | 0.05 | 28 | 87 |
| Isobutyl aldehyde | 0.1 | 20 | 95 |
| Isobutyl aldehyde | 0.2 | 5 | 97 |
| Not added | — | 9 | 58 |

EXAMPLE 5

Forty milliliters of a culture medium composed of 3% soluble starch, 0.1% Proflo (Traders Oil Co., U.S.A.), 0.2% ammonium chloride, 0.05% magnesium sulfate, 1.09% potassium dihydrogen phosphate, 2.09% dipotassium hydrogen phosphate, 0.001% ferrous sulfate and 0.05% isobutyl alcohol were inoculated with 2 ml of the seed culture as of Example 1, and the cultivation was carried out at 28° C. for 8 days.

After the cultivation, it was found that the total production amount of Antibiotic C-15003 was 38 mg/l, and P-3 was produced at a ratio of about 95% (weight/weight).

EXAMPLE 6

To 95 l of the culture broth obtained in Example 2 were added 50 l of acetone, the mixture was stirred for 30 minutes, and to the resultant were added 2 kg of Hyflo Super Cel (Johnes and Manville Products, U.S.A.). After thorough mixing, the mixture was filtered under a pressure to obtain 120 l of filtrate. To the filtrate were added 50 l of water and 90 l of ethyl acetate and the mixture was subjected to extraction. This procedure was repeated twice again. The ethyl acetate layers were pooled, washed twice with 30-l portions of water, dried by the addition of 1 kg of anhydrous sodium sulfate and concentrated under reduced pressure to give 200 ml. Petroleum ether was added to the concentrate and the resultant precipitate was recovered by filtration (58 g). This crude product was stirred with 50 ml of ethyl acetate and the insolubles were filtered off. The filtrate was stirred with 10 g of silica gel (E. Merck, West Germany, 0.05–0.2 mm) and the ethyl acetate was removed away under reduced pressure. The residue was applied onto the top of a silica gel column (500 ml). Elution was carried out stepwise with 500 ml of n-hexane, 500 ml of n-hexane-ethyl acetate (3:1), 500 ml of n-hexane-ethyl acetate (1:1) and 2 l of ethyl acetate saturated with water. The eluate was collected in 50-ml fractions each, and active fractions were detected as follows:

One milliliter portion of each fraction was concentrated to dryness, and 0.1 ml of ethyl acetate was added to the residue to give a solution. The solution was spotted at 2.5 cm from the bottom edge of a silica gel-glass plate (E. Merck, West Germany, 60 $F_{254}$, 0.25 mm, 20×20) and developed for about 17 cm with a solvent system of ethyl acetate saturated with water. After development, detection of P-3 was carried out under ultraviolet light (2537 Å) (Rf value, about 0.42).

The active fractions were collected and concentrated under reduced pressure to about 20 ml. To this concentrate were added 200 ml of petroleum ether to obtain 1.5 g of crude crystals. The crude crystals thus obtained were dissolved in 20 ml of ethyl acetate under warming, and the solution was cooled, whereby crystals were emerged. Filtration gives 1.4 g of pure crystals of P-3, which shows m.p., 189° to 190° C. (purity 97 w/w %) and elemental analysis (Found) (%), C, 60.10; H, 7.00; N, 4.30; Cl, 5.43.

EXAMPLE 7

In the manner as in Example 3, isobutyl propionate, isobutyl butyrate or isobutyl isobutyrate was added after 42 hour cultivation, and the cultivation was further carried out. The results obtained are shown in Table 8.

TABLE 8

| Additive substance | Concentration (%, v/v) | Total production amount (μg/ml) | Ratio of P-3 (%, w/w) |
| --- | --- | --- | --- |
| Isobutyl propionate | 0.02 | 32.8 | 91 |
| Isobutyl butyrate | 0.05 | 22.0 | 85 |
| Isobutyl isobutyrate | 0.05 | 26.5 | 86 |

What we claim is:

1. A method for producing and accumulating Antibiotic C-15003 P-3 which comprises cultivating a microorganism belonging to the genus Nocardia which is capable of producing Antibiotic C-15003 in a culture medium, said culture medium including a member selected from the group consisting of isobutyl aldehyde, isobutyl alcohol and a fatty acid ester of isobutyl alcohol.

2. A method as claimed in claim 1, wherein the microorganism is Nocardia sp. No. C-15003.

3. A method as claimed in claim 1, wherein said member is isobutyl alcohol.

4. A method as claimed in claim 1, wherein said member is isobutyl aldehyde.

5. A method as claimed in claim 1, wherein said member is a mixture of isobutyl alcohol and isobutyl aldehyde.

6. A method as claimed in claim 1, wherein said member is fatty acid ester of isobutyl alcohol.

* * * * *